United States Patent
Thenuwara et al.

(10) Patent No.: US 8,825,171 B1
(45) Date of Patent: Sep. 2, 2014

(54) IMPACT RESISTANT IMPLANTABLE ANTENNA COIL ASSEMBLY

(71) Applicant: Advanced Bionics LLC, Valencia, CA (US)

(72) Inventors: Chuladatta Thenuwara, Castaic, CA (US); William A. Morgan, Stevenson Ranch, CA (US); Janusz A. Kuzma, Bayview (AU)

(73) Assignee: Advanced Bionics, LLC, Valencia, CA (US)

( * ) Notice: Subject to any disclaimer, the term of this patent is extended or adjusted under 35 U.S.C. 154(b) by 3 days.

(21) Appl. No.: 13/669,193

(22) Filed: Nov. 5, 2012

Related U.S. Application Data

(63) Continuation of application No. 12/326,804, filed on Dec. 2, 2008, now Pat. No. 8,321,028.

(51) Int. Cl.
*A61N 1/08* (2006.01)

(52) U.S. Cl.
USPC ............................................................ 607/60

(58) Field of Classification Search
USPC ............................................................ 607/60
See application file for complete search history.

(56) References Cited

U.S. PATENT DOCUMENTS

| | | | |
|---|---|---|---|
| 4,889,485 A * | 12/1989 | Iida | 433/9 |
| 5,466,247 A | 11/1995 | Scheiner et al. | |
| 5,776,169 A * | 7/1998 | Schroeppel | 607/36 |
| 5,871,530 A * | 2/1999 | Williams et al. | 607/122 |
| 6,358,281 B1 | 3/2002 | Berrang et al. | |
| 6,542,777 B1 | 4/2003 | Griffith et al. | |
| 6,648,914 B2 | 11/2003 | Berrang et al. | |
| 6,931,284 B2 * | 8/2005 | Engmark et al. | 607/36 |
| 7,260,435 B2 | 8/2007 | Ibrahim | |
| 2004/0176673 A1 | 9/2004 | Wahlstrand et al. | |
| 2007/0128940 A1 | 6/2007 | Ho et al. | |
| 2008/0046034 A1 | 2/2008 | Ibrahim | |
| 2008/0046040 A1 | 2/2008 | Denker et al. | |
| 2008/0183263 A1 * | 7/2008 | Alexander | 607/122 |
| 2009/0069892 A1 | 3/2009 | Zimmerling et al. | |
| 2009/0143839 A1 | 6/2009 | Zimmerling | |
| 2010/0204768 A1 | 8/2010 | Jolly et al. | |

FOREIGN PATENT DOCUMENTS

| | | |
|---|---|---|
| WO | 9323113 | 11/1993 |
| WO | 02003226 A2 | 7/2002 |
| WO | 02003226 A3 | 7/2002 |
| WO | 03039656 | 5/2003 |
| WO | 2005005363 A1 | 6/2005 |
| WO | 2006026687 A2 | 3/2006 |
| WO | 2006026687 A3 | 3/2006 |
| WO | 2009036006 A1 | 3/2006 |
| WO | 2009036006 A4 | 3/2006 |
| WO | 2010091237 A2 | 8/2010 |
| WO | 2010091237 A3 | 8/2010 |

* cited by examiner

*Primary Examiner* — Michael Kahelin
(74) *Attorney, Agent, or Firm* — Steven L. Nichols; Van Cott, Bagley, Cornwall & McCarthy P.C.

(57) ABSTRACT

An impact resistant implantable antenna coil assembly comprising a flat antenna coil having a plurality of laterally separated turns of wire encapsulated with a non-orthogonal force absorbing coil reinforcement in a flexible biocompatible polymer and axially anchored with the reinforcement to a feedthrough case. Thus configured, non-orthogonal impact forces applied to the antenna coil assembly are absorbed and lateral components thereof that would otherwise be reflected as tensile forces in the plane of the coil are prevented from forming or from fracturing wire within the antenna coil.

22 Claims, 9 Drawing Sheets

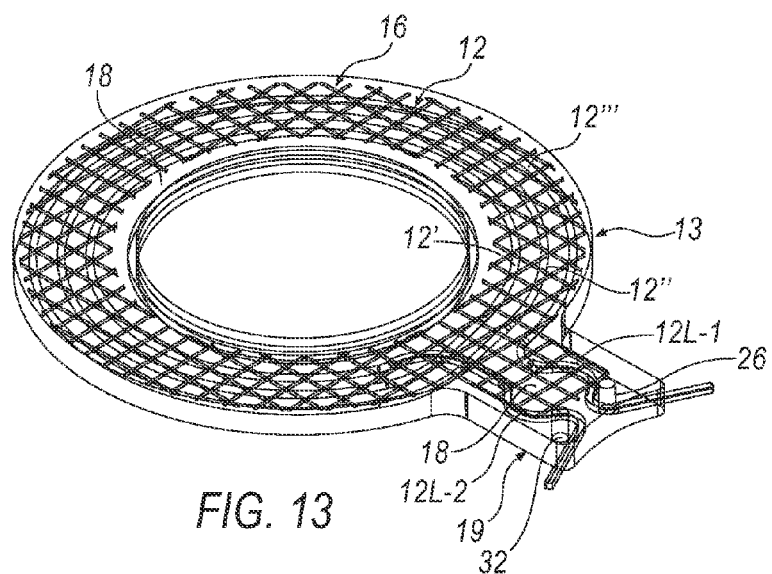
FIG. 13
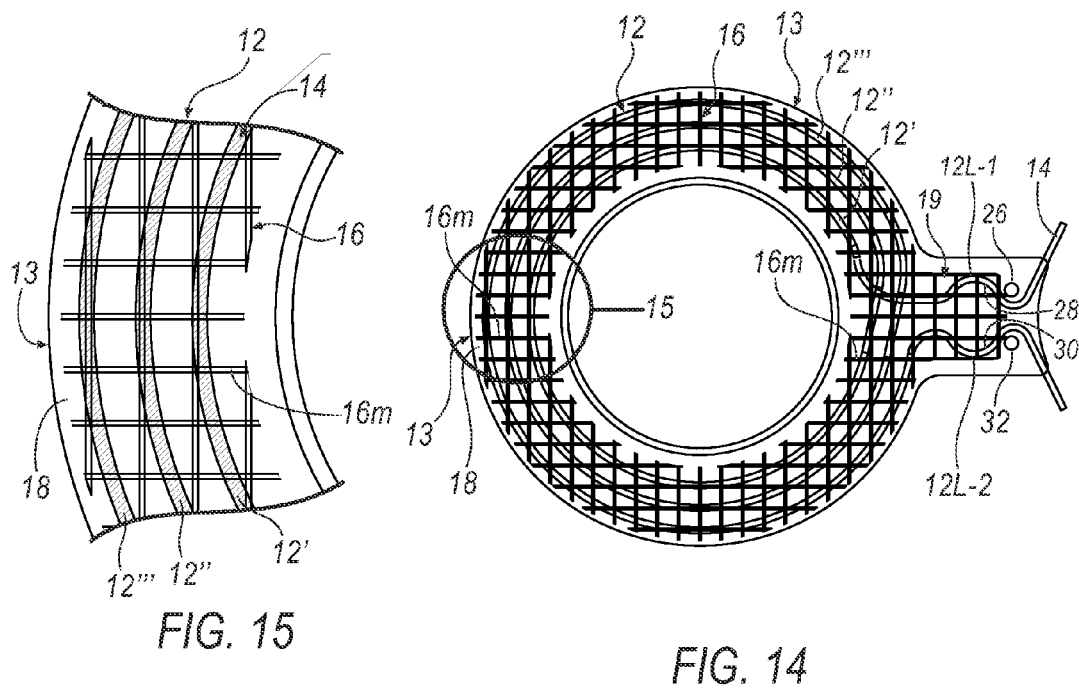
FIG. 15
FIG. 14

IMPACT RESISTANT IMPLANTABLE ANTENNA COIL ASSEMBLY

RELATED DOCUMENTS

The present application is a continuation, and claims the benefit under 35 U.S.C. §120, of U.S. application Ser. No. 12/326,804, filed Dec. 2, 2008, now U.S. Pat. No. 8,321,028. This application is hereby incorporated by reference in its entirety.

FIELD OF INVENTION

The present invention relates to implantable medical devices and, more particularly, to an improved impact resistant implantable antenna coil assembly for an implantable cochlear stimulator system.

BACKGROUND OF INVENTION

Implanted medical devices are sometimes subjected to impact from externally applied forces, such as those associated with the falling of a patient or a blow to the patient's body in the region of the implanted medical device. While most externally applied forces do not result in damage to or failure of an implanted medical device, implanted medical devices including an antenna coil assembly such as that of a cochlear implant, are known to have been damaged by impact forces to the head of the patient where such implants are located. Such failed devices are surgically removed and replaced with a functioning device, and examined to determine the failure mechanism. Applicants' examination of such removed devices has revealed that the failure mechanism was commonly a tensile breakage of wire in the implanted antenna coil assembly. Further analysis by the applicants has revealed that the wire breakage was the result of impact forces, especially forces non-orthogonal to the plane of the implanted antenna coil assembly. Such non-orthogonal impact forces included lateral components reflected as tensile forces in the plane of the coil assembly sufficient to fracture the wire. Such impact forces may result from a fall or a glancing blow where the impact is made non-orthogonal to (i.e., other than normal to) the head. Because these devices are implanted subcutaneously, the impact resistance of the device is at least in part dependant upon the thickness of the skin flap that covers the device. While thicker skin flaps of adults afford some impact protection, children often have skin flaps of only 1 to 3 mm, and therefore are at more risk of breaking the coil wire.

U.S. Pat. No. 6,542,777, issued Apr. 1, 2003, which is assigned to the assignee of the present invention and incorporated herein by reference, describes and illustrates an invention directed to the use of a spiral shield that improves the electrical behavior of an implantable secondary coil of an implantable device. To maintain the spacing of the turns of the secondary coil during the manufacturing process, a polymeric spacer is placed between adjacent turns. The coil, spacer, and shield then are encapsulated in a biocompatible polymer, which is preferably the same polymer used for the spacer (column 2, lines 42-45 and column 3, lines 23-27), or a material with similar physical characteristics (column 5, lines 40-43), with examples given as SILASTIC® or SILBIONE® LSR 70 (column 6, lines 8-12). At column 3, lines 16-23, the '777 patent states that the combination of the biocompatible polymer encapsulation, multi-strand wire, and spiral shield results in a thin, flexible, secondary coil assembly that resists damage from impacts. While that may be true, there is no teaching or suggestion in the '777 patent of any means for absorbing non-orthogonal impact forces. Because the spacers are made from the same material or a material with similar physical characteristics as the encapsulant, such as 70 durometer silicone rubber, the overall structure is uniform, and the final molding is the same whether manufactured with or without spacers. Further, applicants have found that such a silicone encapsulated secondary coil assembly may be subject to non-orthogonal impact forces having lateral components reflected as tensile forces in the plane of the coil assembly sufficient to fracture the coil wires within the antenna coil assembly.

Accordingly, there is an immediate and continuing need for an improved impact resistant implantable antenna coil assembly for medical devices that will absorb non-orthogonal impact forces and particularly the lateral components thereof that would otherwise be reflected as tensile forces in the plane of the coil capable of fracturing the wire. The present invention satisfies that need.

SUMMARY OF INVENTION

The present invention comprises an improved impact resistant implantable antenna coil assembly for a medical device, such as an implantable cochlear stimulator. The coil assembly comprises a flat antenna coil having a plurality of laterally separated turns of wire encapsulated with a non-orthogonal force absorbing reinforcement in a flexible, biocompatible polymer forming a flat case for the antenna coil, referred to as a "coil case".

The wire of the antenna coil preferably comprises multiple filaments that may be twisted together to form a strand; multiple strands may be twisted or wound together to form a wire cable or rope. Alternatively, the wire may be braided or in another multifilament configuration. Whether multiple stranded filaments or cabled strands, or other configuration, the term "wire" will be used hereinafter to refer to the antenna coil wire of any of the foregoing constructions.

The reinforcement against non-orthogonal impact forces is preferably formed of a polymeric material and is anchored and encapsulated within the coil case adjacent the antenna coil. Thus configured, non-orthogonal impact forces applied to the antenna coil case are absorbed by the reinforcement, and lateral components thereof that would otherwise be reflected as tensile forces in the plane of the coil are prevented from forming or from fracturing wire within the antenna coil. Similarly, normal forces or the normal component of non-orthogonal forces will cause the coil assembly to expand radially outward, inducing hoop stress loading, resulting in tensile failure of the wire.

By way of example only, the anchored reinforcement may comprise a polyester or polypropylene mesh or fibers embedded in the encapsulation, or polyester or polypropylene fibers forming a braid around, or bundle or core upon which the wire comprising the antenna coil is wound or, preferably, polyethylene fibers that may be placed alongside and between the turns of the antenna coil, or equivalents or combinations of the foregoing.

Further, the antenna coil assembly may comprise an attachment for the reinforcement and for the wires of the antenna coil outside the coil case such as within a feedthrough case adjacent the coil case. By way of example, the feedthrough case may comprise a base of polymeric material having guide channels for ends of the coil wire extending from the encapsulation in the coil case and separate anchors for the reinforcement. The guide channels may include laterally outward extending loops in the plane of the coil case adjacent anchored ends of the coil wire for relieving axial forces in the coil wire while the anchors for the reinforcement may comprise end and/or side supports for a reinforcing mesh comprising the reinforcement or eyelets or various clamping structures for ends of polyester or polyethylene fibers or fiber strands or bundles comprising the reinforcement and extending from the encapsulation in the coil case.

The foregoing structures as well as other structures and features of the present invention may be more fully understood by reference to the following detailed description referring to the drawings briefly described as follows.

BRIEF DESCRIPTION OF DRAWINGS

FIG. 13 is a perspective view of an illustrative antenna assembly according to a fourth embodiment of the principles described herein.

FIG. 14 is a top view of the antenna assembly of FIG. 13.

FIG. 15 is an enlarged top view of the portion of the coil assembly within the circle 15 in FIG. 14.

DETAILED DESCRIPTION OF INVENTION

Figure 1:
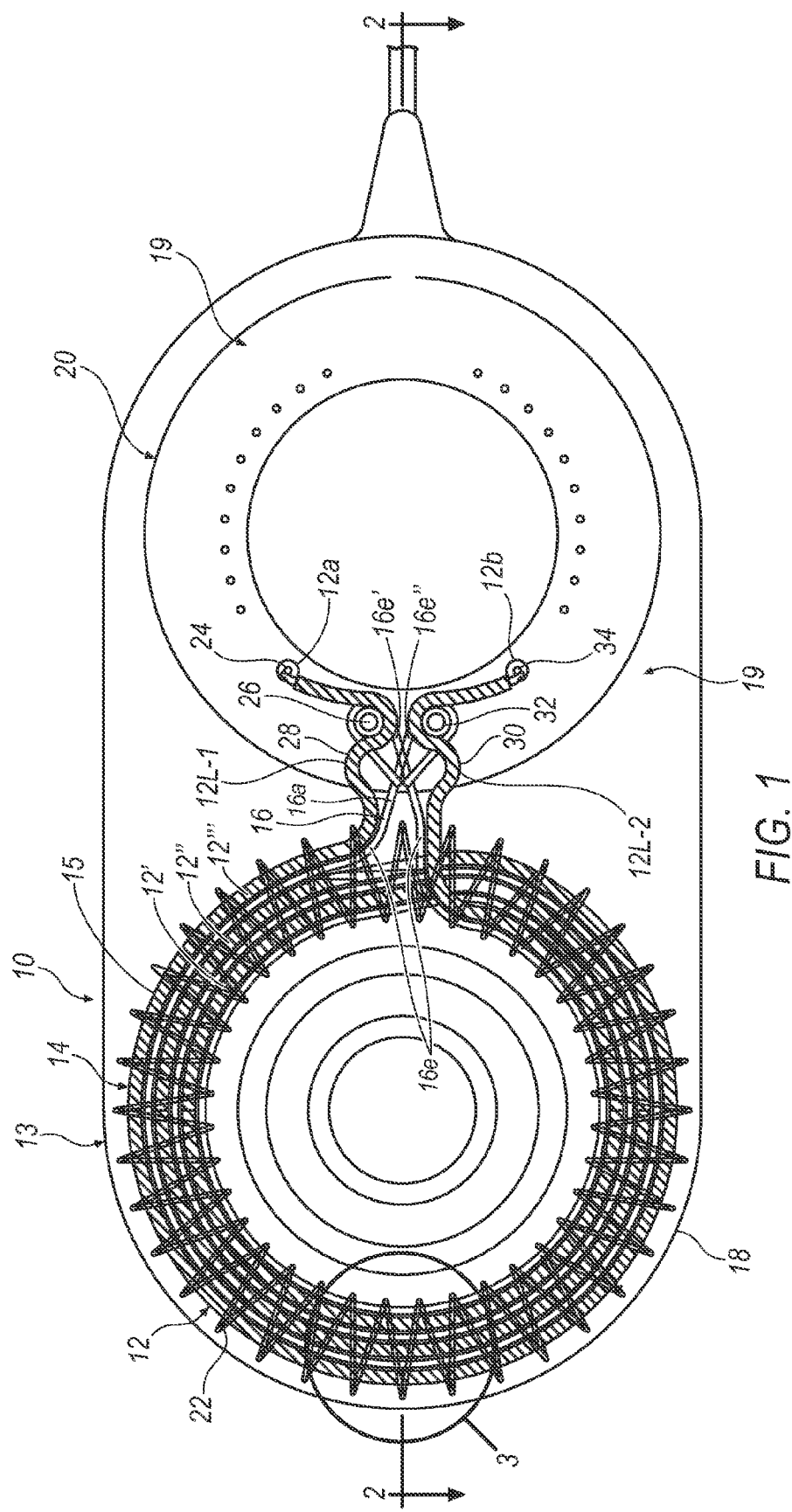
FIG. 1 is a top view of an illustrative antenna assembly according to a first embodiment of the principles described herein

As shown in the figures, the present invention generally comprises an improved impact resistant implantable antenna coil assembly 10 for an implantable medical device, such as a cochlear stimulator system for subcutaneous implant. The antenna assembly 10 comprises a flat antenna coil 12 located in a flat, low profile, protective, flexible coil case 13 of a biocompatible material 18, such as silicone. The illustrated versions of the antenna coil 12 have a plurality of laterally separated turns, e.g. 12', 12" and 12'" of wire 14, preferably in the form of a multifilament strand made of a high concentration of a noble metal such as gold. As shown in each of the several following preferred embodiments, the antenna coil 12, along with a non-orthogonal force absorbing reinforcement 16, is encapsulated within a flexible biocompatible polymer 18 forming the coil case 13. Further, in each of the several following embodiments, the wire 14 of the antenna coil 12 and the reinforcement 16 are axially secured within the coil case 13 and to an attachment 19 preferably comprising an adjacent feedthrough case 20.

As will be described in detail hereinafter, with the antenna coil assembly 10 thus configured and secured, non-orthogonal impact forces applied to the antenna coil assembly are absorbed by the reinforcement 16, and lateral components thereof that would otherwise be reflected as tensile forces in the plane of the antenna coil 12 are prevented from forming or from fracturing wire within the antenna coil 12.

The first of several embodiments of the present invention possessing the foregoing non-orthogonal impact force resistant features is illustrated in FIGS. 1-5. As depicted most clearly in FIGS. 1, 3, and 5, the antenna coil 12 of the antenna assembly 10 comprises multifilament metallic filaments wrapped into a wire 14 housed in a lumen of tubing of polymeric material, such as a silicone tube 15. The wire 14 is formed into three turns 12', 12" and 12'" that are collectively received within or surrounded by a wound and partially flattened metal shield 22. The shield 22 functions to confine the electrical field of the coil 12 preventing capacitive coupling of the coil through tissue covering the coil as described in U.S. Pat. No. 6,542,777.

As illustrated most clearly in FIG. 1, a first free end 12a of the coil 12 extends from a vertically extending feedthrough pin 24 in the feedthrough case 20. The free end 12a is electrically and axially secured to the pin 24, as by welding. From the pin 24, the coil 12 extends around an anchoring post 26 into an outward laterally extending guide loop 28 in a base of the feedthrough case 20. From there, it enters the silicone tube 15 and forms the outermost turn 12'", then the middle turn 12", and then the innermost turn 12' in the coil case 13, where it exits the silicone tube 15 and returns to the feedthrough case 20. Within the feedthrough case 20, the turn 12' is guided by an outward laterally extending guide loop 30 in the feedthrough case 20 around an anchoring post 32 to a vertically extending feedthrough pin 34 to which a second end 12b of the coil 12 is electrically and axially secured as by welding. The guide loops 28 and 30 introduce corresponding service loops 12L-1 and 12L-2 into the coil 12 that provide axial slack in the wire 14, allowing some longitudinal movement of the wire 14 within the silicone tube 15 and within the feedthrough case 20 in response to any tensile forces applied to the coil by an externally applied non-orthogonal impact force. This ability of the wire 14 to move with respect to the silicone tube 15 also makes the overall structure more flexible than it would be were the wire 14 to be directly encapsulated by polymer 18; this flexibility greatly facilitates implanting the device.

Figure 3:
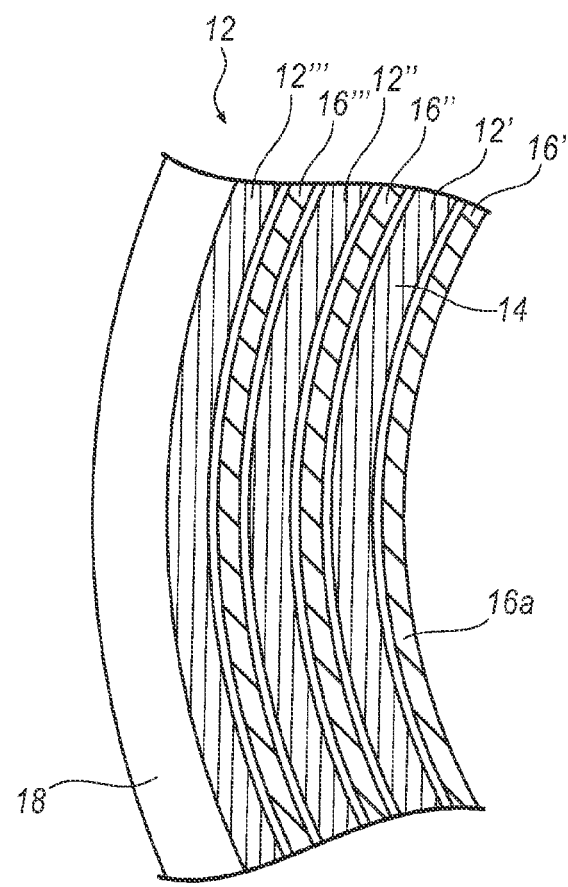
FIG. 3 is a top view of the portion of the structure of the antenna assembly of FIG. 1 within a circle 3 in FIG. 1.
Figure 4:
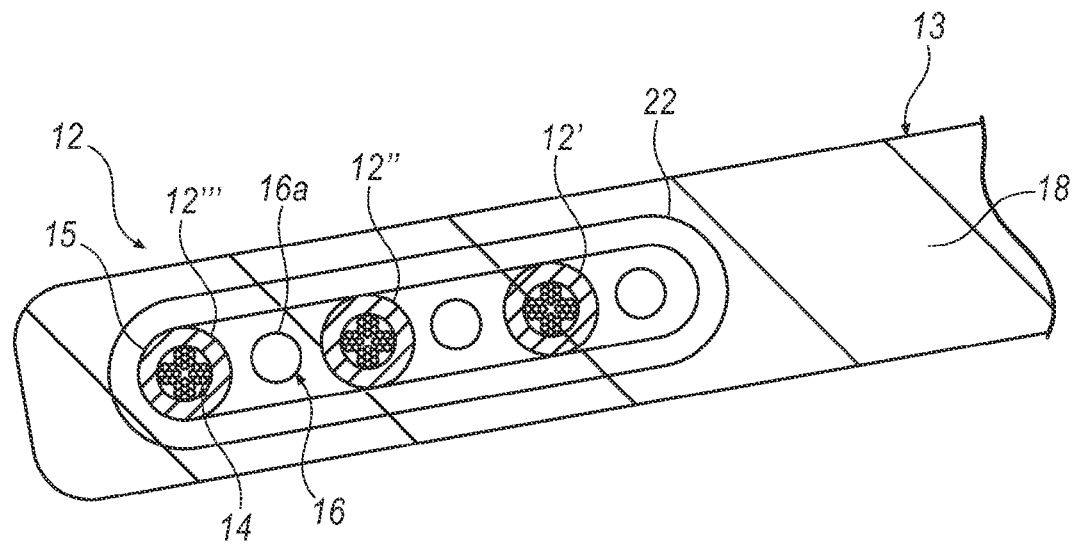
FIG. 4 is an enlarged cross-sectional side view of the portion of the antenna coil and non-orthogonal force absorbing reinforcement in the antenna assembly of FIG. 1 lying within a circle 3 in FIG. 1.
Figure 5:
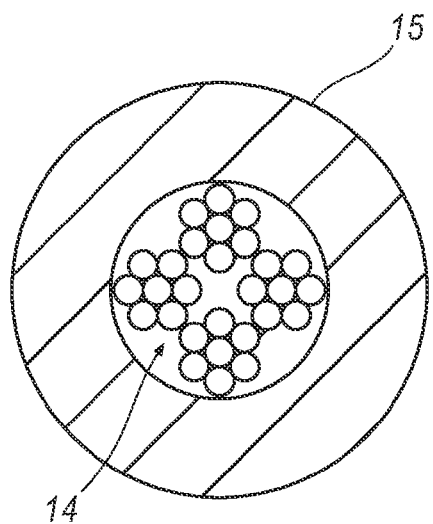
FIG. 5 is an enlarged cross-section of the antenna assembly of FIG. 1 showing the antenna coil wire within a lumen of polymeric tubing.

As illustrated most clearly in FIGS. 1, 3, and 4, the first non-orthogonal force absorbing reinforcement 16 of the first embodiment of the antenna coil assembly 10 of the present invention may comprise longitudinally extending fibers of a polymeric material having a high tensile strength (e.g., configured to withstand 12 pounds axial force) and low dielectric constant, such as polyethylene (having a dielectric constant of ~2.3) or polypropylene (having a dielectric constant of ~2.2). The fibers may be any configuration, such as side-by-side, twisted, or braided, but are preferably oriented to provide high axial tensile strength without stretching, and are encapsulated and thereby locked into the polymer 18 to provide resistance of the overall structure to local stretching along the axis of the fiber.

In addition to their being secured within polymer 18 along their length, the fibers are preferably additionally secured on their ends to an attachment 19, to provide resistance of the overall structure to global stretching along the fiber axis. A preferred material for reinforcement 16 is Ultra High Molecular Weight Polyethylene (8 ends of 55 dtex braided) which is strong, has very low elongation, and is biocompatible. Preferably, such polyethylene fibers are twisted or braided with a low stitch count into an elongated bundle 16a that resists axial stretching and extends longitudinally in the same direction as the coil 12 between and spaced laterally from its turns 12', 12", and 12'", oriented generally parallel to wire 14. As shown, free ends 16e' and 16e" of the bundle 16a extend from the coil case 13 to the feedthrough case 20. There, the end 16e' wraps around the anchoring post 26 while the end 16e" wraps around the anchoring post 32 to meet and anchor with the end 16e' within the encapsulating polymer 18. Thus contained, the bundle 16a is axially secured against stretching within the coil case 13 and within the feedthrough case 20 even during the application of non-orthogonal impact forces having lateral components in the plane of the antenna coil 12 and reflected as longitudinal tensile forces in the bundle 16a.

Figure 6:
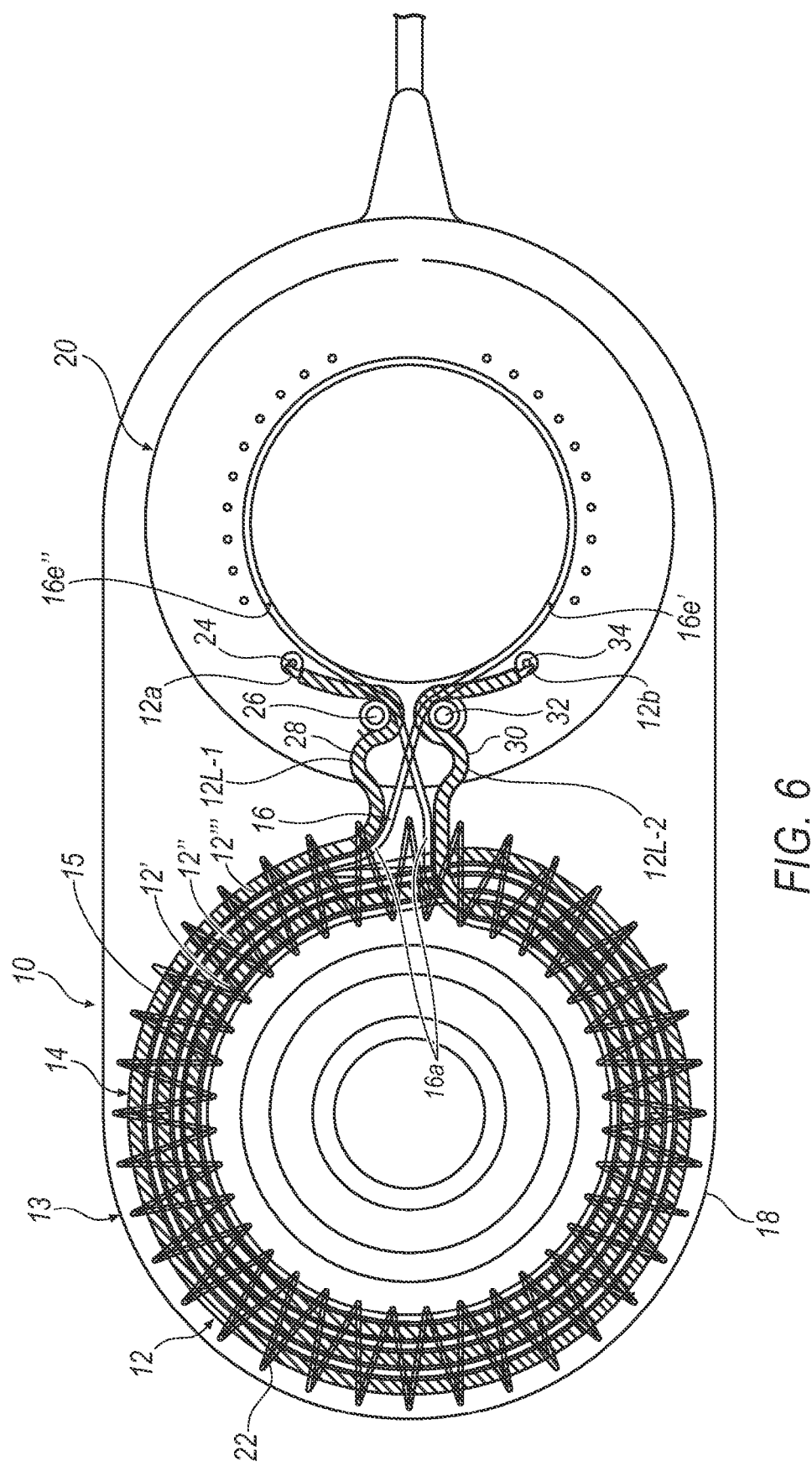
FIG. 6 is a top view of the antenna assembly of FIG. 1 illustrating an alternate manner of axially securing ends of the illustrated non-orthogonal force absorbing reinforcement within the feedthrough case comprising the attachment of the antenna assembly.

An alternate method of anchoring the ends 16e' and 16e" of the bundle 16a in the feedthrough case 20 is illustrated in FIG. 6. The end 16e' of the fiber bundle 16a extends from the coil case 13 from a location radially inside the coil turn 12' into the feedthrough case 13 around the anchoring post 26 where it wraps around the feedthrough case clockwise to terminate adjacent the feedthrough pin 34. The end 16e" of the fiber bundle 16a extends from the coil case 13 between the coil turns 12" and 12'" into the feedthrough case 20, around the anchoring post 32 and wraps around the feedthrough case counterclockwise over the end 16e', to terminate adjacent the feedthrough pin 24 within the encapsulating polymer 18. Thus contained, the bundle 16a is axially secured against stretching within the coil case 13 and within the feedthrough case 20 even during the application of non-orthogonal impact forces having lateral components in the plane of the antenna coil 12 and reflected as longitudinal tensile forces in the bundle 16a.

Figure 2:
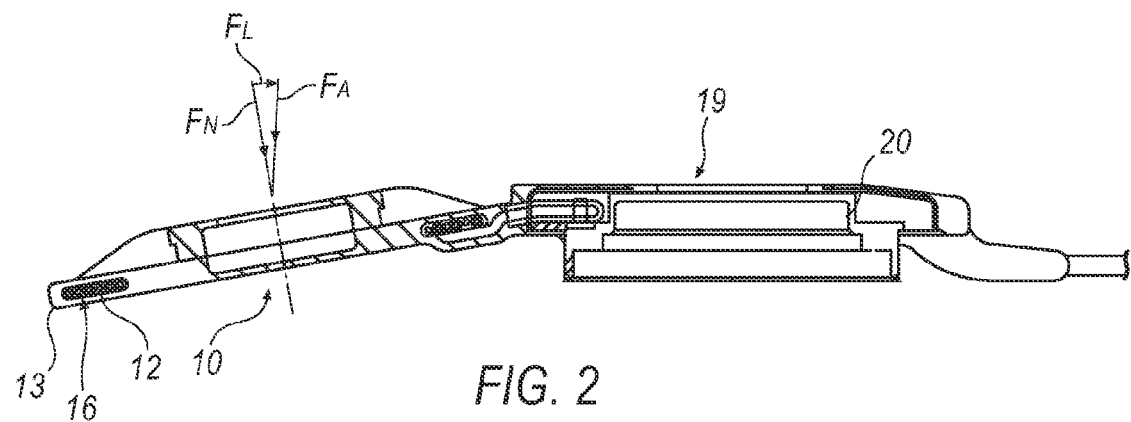
FIG. 2 is a sectional side view of the antenna assembly of FIG. 1 along the line 2-2 in FIG. 1 including a diagrammatic illustration of an impact force vector that is non-orthogonal to the plane of the antenna coil

Because the bundle 16a of the first embodiment of the reinforcement 16 of antenna coil assembly 10 and the individual fibers thereof are encapsulated within the polymer 18 and axially secured against stretching within the coil case 13 and within the feedthrough case 20 comprising the attachment 19, the bundle 16a and its component fibers resist axial movement in response to the lateral components of non-orthogonal impact forces applied to the assembly 10 as diagrammatically depicted in FIG. 2. As there illustrated, a non-orthogonal, or non-normal, impact force $F_A$ is applied to the antenna case 13. The non-orthogonal impact force $F_A$ comprises a lateral component $F_L$ and a normal component $F_N$. The lateral component $F_L$ is reflected in the plane of the coil 12 as a tensile force that might be capable of fracturing or breaking the antenna coil wire 14. However, in the antenna coil assembly 10 of the present invention, that lateral force component is absorbed by the reinforcement 16 encapsulated with the antenna coil 12 within the coil case 13. Specifically, in the first embodiment of the antenna coil assembly 10 illustrated and described above relative to FIGS. 1-6, the reinforcement 16 comprising the bundle 16a is structured and secured to resist axial movement within the coil case 13 whereas the antenna coil 12 is structured to allow some longitudinal movement within the coil case 13, by allowing movement of wire 14 within the silicone tube 15, and within the feedthrough case 20, by virtue of the service loops 12L-1 and 12L-2. Therefore, by virtue of its previously described internal structure and its local encapsulation and axial anchoring within the coil case 13 and its global encapsulation and anchoring within the coil case 13 and the attachment 19, the reinforcement 16 of the first embodiment of the antenna coil assembly 10 responds to non-orthogonal impact forces ($F_A$) applied to the antenna coil assembly 10 by absorbing the lateral tensile force components thereof ($F_L$) that might otherwise be capable of fracturing or breaking the wire 14 of the antenna coil 12.

Figure 7:
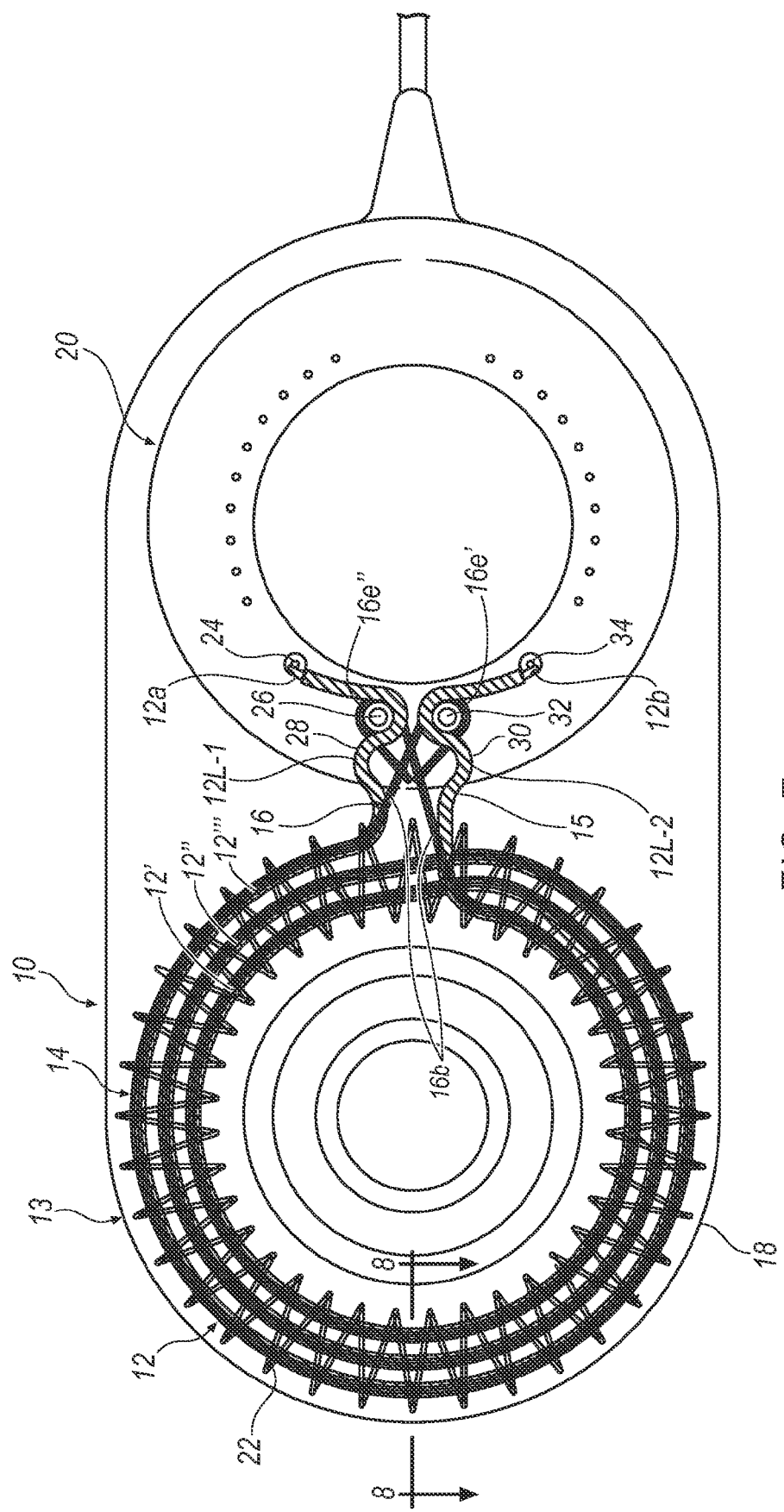
FIG. 7 is a top view of an illustrative antenna assembly according a second embodiment of the principles described herein.
Figure 8:
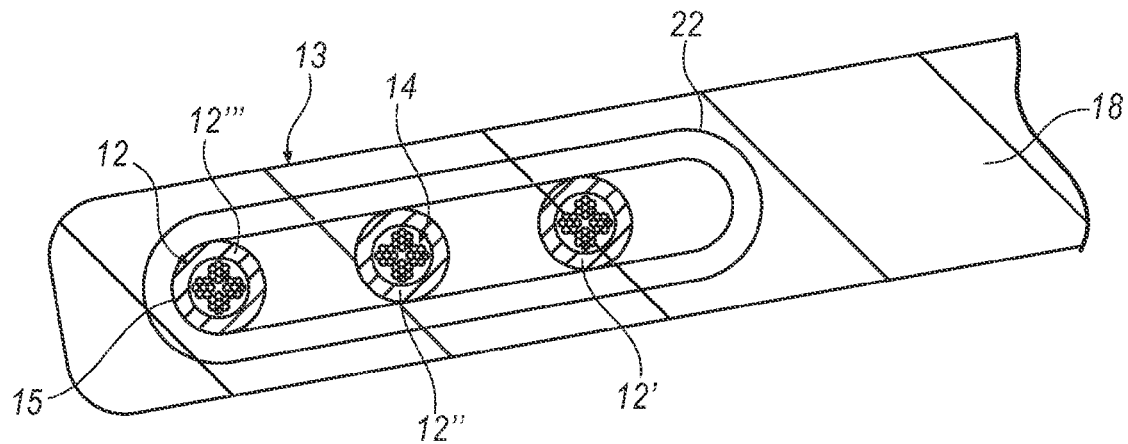
FIG. 8 is an enlarged fragmentary cross-sectional view of the antenna coil and the reinforcement along the line 8-8 in FIG. 7.
Figure 9:
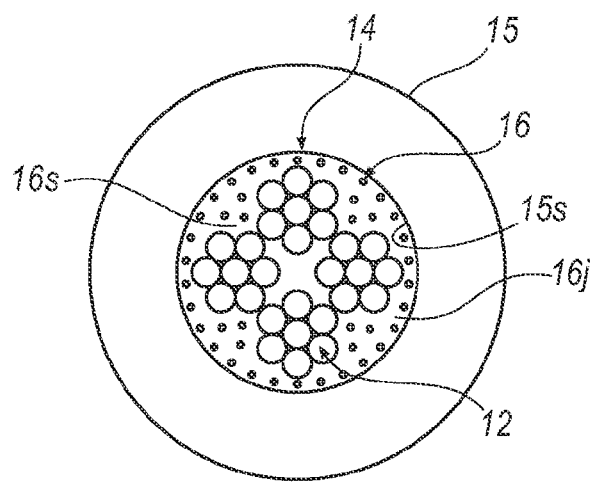
FIG. 9 is an enlarged cross-sectional view of the antenna assembly of FIG. 7 showing the antenna coil wire with the reinforcing fibers alongside of and over the wire inside of a tube of polymeric material.

The second of the several embodiments of the present invention possessing the foregoing non-orthogonal impact force resistant features is illustrated in FIGS. 7-9 and will be described using the same reference numerals previously used for similar structural elements of the first embodiment. The antenna coil 12 of the second antenna assembly 10 preferably comprises multifilament metallic wire wrapped or braided into the wire 14 comprising the antenna coil housed in the silicone tube 15 and formed into the three turns 12', 12", and 12'" that are collectively received within or surrounded by the metal shield 22.

In a manner nearly identical to that illustrated in FIG. 1 for the first embodiment of the antenna coil assembly 10, in the second embodiment illustrated in FIG. 7, the first free end 12a of the wire 14 extends from the vertical feedthrough pin 24 in the feedthrough case 20 where it is electrically and axially secured to the pin 24 as by welding. From the pin 24, the wire 14 of the antenna coil 12 extends around the anchoring post 26 into the outward laterally extending guide loop 28 in a base of the feedthrough case 20 to form the coil loop 12L-1 that provides axial slack in the coil allowing some longitudinal movement of the coil 12 within the feedthrough case 20 in response to any tensile forces applied to the coil by an externally applied non-orthogonal impact force. Then, housed in the silicone tube 15, the wire 14 forms the outermost turn 12'", spirals inwardly forming the middle turn 12", and then the innermost turn 12', where it exits the silicone tube 15 and returns to the feedthrough case 20. Within the feedthrough case 20, the wire 14 in turn 12' is guided by the outward laterally extending guide loop 30 in the feedthrough case 20 to form the coil loop 12L-2 that provides axial slack in the coil allowing some longitudinal movement of the coil 12 within the silicone tube 15 and within the feedthrough case 20 in response to any tensile forces applied to the coil by an externally applied non-orthogonal impact force. From the loop 12L-2, the wire 14 loops around the anchoring post 32 to the vertical feedthrough pin 34 to which the second end 12b of the coil 12 is electrically and axially secured as by welding.

As illustrated most clearly in FIGS. 7 and 9, the second non-orthogonal force absorbing reinforcement 16 of the second embodiment of the antenna coil assembly 10 of the present invention comprises an elongated bundle 16b of longitudinally extending fibers of a polymeric material, such as polyethylene, located in radial outward spaces 16s between the filaments of the wire 14, and polyethylene fibers wound or braided into a longitudinally extending sleeve or jacket 16j receiving and radially confining the wire 14 of the antenna coil 12 within the silicone tube 15 at an inner surface 15s thereof as represented in FIG. 9.

As depicted in FIG. 7, the elongated bundle 16b separates from the wire 14 of the coil 12 in the turns 12''' and 12' between the coil case 13 and the feedthrough case 20. Following that separation, the end 16e'' of the bundle 16b extends longitudinally from turn 12''' and wraps around the anchoring post 32. Similarly, the end 16e' of the bundle 16b extends longitudinally from turn 12' and wraps around the anchoring post 26. The ends 16e' and 16e'' engage and are secured in the encapsulation 18 extending into the feedthrough case 20.

Because the bundle 16b of the second embodiment of the reinforcement 16 of antenna coil assembly 10 and the individual fibers thereof are encapsulated within the polymer 18 and axially secured against stretching within the coil case 13 and within the feedthrough case 20 comprising the attachment 19 and because the bundle 16b and its component fibers are reinforced by the protective sleeve or jacket 16s, the bundle 16b resists axial movement in response to the lateral components of non-orthogonal impact forces applied to the assembly 10 as diagrammatically depicted in FIG. 2. As there illustrated, a non-orthogonal impact force $F_A$ is applied to the antenna case 13. The non-orthogonal impact force $F_A$ comprises a lateral component $F_L$ and a normal component $F_N$. The lateral component $F_L$ is reflected in the plane of the coil 12 as a tensile force that might be capable of fracturing or breaking the antenna coil wire 14. However, in the antenna coil assembly 10 of the present invention, that lateral force component is absorbed by the reinforcement 16 encapsulated with the antenna coil 12 within the coil case 13. Specifically, in the second embodiment of the antenna coil assembly 10 illustrated and described above relative to FIGS. 7-9, the reinforcement 16 comprising the bundle 16b is structured and secured to resist axial movement within the coil case 13 whereas the wire 14 of the antenna coil 12 is structured and allowed by the reinforcement some longitudinal movement within the coil case 13 and silicone tube 15 and within the feedthrough case 20. Therefore, by virtue of its previously described internal structure and its local encapsulation and axial anchoring within the coil case 13, and its global encapsulation and anchoring within the coil case 13 and the attachment 19, the reinforcement 16 of the second embodiment of the antenna coil assembly 10 responds to non-orthogonal impact forces ($F_A$) applied to the antenna coil assembly 10 by absorbing the lateral tensile force components thereof ($F_L$) that might otherwise be capable of fracturing or breaking the wire 14 of the antenna coil 12.

Figure 10:
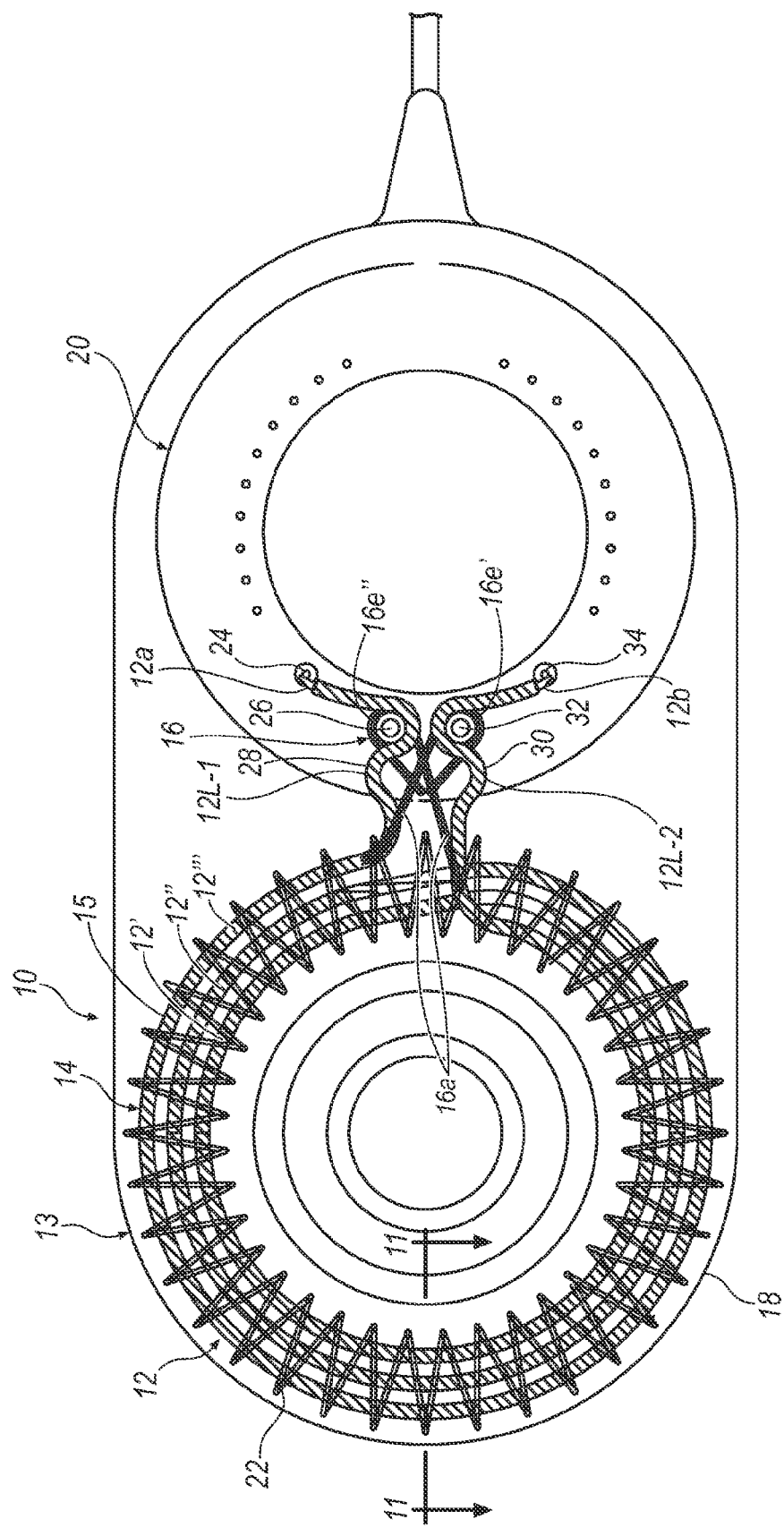
FIG. 10 is a top view of an illustrative antenna assembly according to a third embodiment of the principles described herein.
Figure 11:
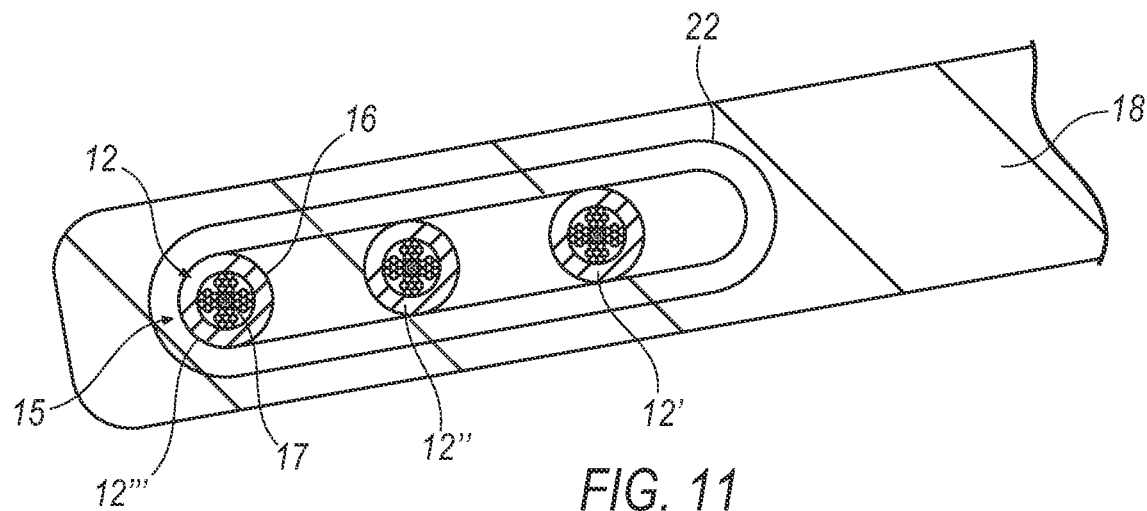
FIG. 11 is an enlarged fragmentary cross-sectional view of the antenna coil assembly and reinforcement of FIG. 10 along the line 11-11 in FIG. 10.
Figure 12:
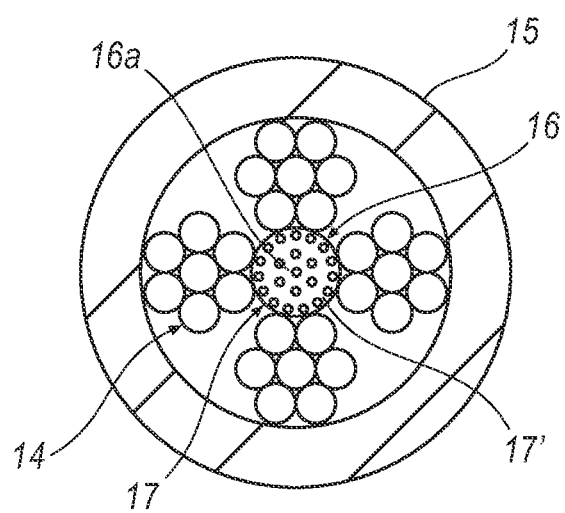
FIG. 12 is an enlarged cross-sectional view of the antenna assembly of FIG. 10 showing the antenna coil wire wrapped around the centrally-located and axially-extending core of reinforcing fiber strands or bundles of the reinforcement within a lumen of a tube of biocompatible polymeric material.

The third of the several embodiments of the present invention possessing the non-orthogonal impact force resistant features is illustrated in FIGS. 10-12 and will be described using the same reference numerals previously used for similar structural elements of the first embodiment. As depicted most clearly in FIGS. 10 and 11, the antenna coil 12 of the third antenna assembly 10 comprises multiple wire strands or filaments wrapped around a central core 17 of polymeric fiber strands or bundles 16a to form the wire 14. The central core 17 comprises a third preferred form of a non-orthogonal force absorbing reinforcement 16 and the wire and central core are encapsulated and axially secured in the polymeric material 18 forming the coil case 13 with ends of the antenna coil 12 and the reinforcement 16 being axially secured in an attachment 19 comprising the feedthrough case 20. The multifilament metallic wire 14 is housed in the silicone tube 15 and formed into three turns 12', 12'' and 12''' that are collectively received within or surrounded by the wound, metal shield 22.

In a manner nearly identical to that illustrated in FIGS. 1 and 7 for the first and second embodiments of the antenna coil assembly 10, in the third embodiment illustrated in FIG. 10, the first free end 12a of the wire 14 of the coil 12 extends from the vertical feedthrough pin 24 in the feedthrough case 20 where it is electrically and axially secured to the pin 24 as by welding. From the pin 24, the coil 12 extends around the anchoring post 26 into the outward laterally extending guide loop 28 in a base of the feedthrough case 20 to form the coil loop 12L-1 that provides axial slack in the coil allowing some longitudinal movement of the coil 12 within the feedthrough case 20 in response to any tensile forces applied to the coil by an externally applied non-orthogonal impact force. Then, housed in the silicone tube 15, the coil 12 forms the outermost turn 12''', spirals inwardly forming the middle turn 12'', and then the innermost turn 12', where it returns to the feedthrough case 20. Within the feedthrough case 20, the multifilament metallic wire 14 in turn 12' is guided by the outward laterally extending guide loop 30 in the feedthrough case 20 to form the coil loop 12L-2 that provides axial slack in the coil allowing some longitudinal movement of the coil 12 within the silicone tube 15 and within the feedthrough case 20 in response to any tensile forces applied to the coil by an externally applied non-orthogonal impact force. From the loop 12L-2, the wire 14 loops around the anchoring post 32 around the anchoring post 32 to the vertical feedthrough pin 34 to which the second end 12b of the coil 12 is electrically and axially secured as by welding.

As illustrated most clearly in FIGS. 10 and 12, the third non-orthogonal force absorbing reinforcement 16 of the third embodiment of the antenna coil assembly 10 of the present invention comprises the core 17 formed of the fiber bundle 16a of longitudinally extending fibers of a polymeric material such as polyethylene encapsulated in a polymeric material 17', such as silicone. Thus configured, the force absorbing reinforcement 16 of the third embodiment forms the central core 17 within the silicone tube 17' around which the multifilament metallic wire 14 of the antenna coil is wrapped as represented in FIG. 12.

As depicted in FIG. 10, the elongated bundle 16a in the turns 12''' and 12' separate from the wires of the coil 12 before reaching the feedthrough case 20. Following that separation, the bundle 16a from turn 12''' extends longitudinally and wraps around the anchoring post 32. Similarly, the bundle 16a from turn 12' extends longitudinally and wraps around the anchoring post 26 where the end 16e'' engages and is secured in the encapsulation 18 relative to the bundle 16a in the end 16e'.

Because the bundles 16a of the third embodiment of the reinforcement 16 of antenna coil assembly 10 and the individual fibers thereof are encapsulated within the polymer 18 and axially secured against stretching within the coil case 13 and within the feedthrough case 20 comprising the attachment 19, the bundles 16a resist axial movement in response to the lateral components of non-orthogonal impact forces applied to the assembly 10 as diagrammatically depicted in FIG. 2. As previously described and illustrated, a non-orthogonal impact force $F_A$ is applied to the antenna case 13. The non-orthogonal impact force $F_A$ comprises a lateral component $F_L$ and a normal component $F_N$. The lateral component $F_L$ is reflected in the plane of the coil 12 as a tensile force that might be capable of fracturing or breaking the antenna coil wire. However, in the antenna coil assembly 10 of the present invention, that lateral force component is absorbed by the reinforcement 16 encapsulated with the antenna coil 12 within the coil case 13. Specifically, in the third embodiment of the antenna coil assembly 10 illustrated and described above relative to FIGS. 10-12, the reinforcement 16 comprising the bundle 16a is structured and secured to resist axial movement within the coil case 13 whereas the antenna coil 12 is structured and allowed by the reinforcement some longitudinal movement within the coil case 13 and silicone tube 15 and within the feedthrough case 20. Therefore, by virtue of its previously described internal structure and its local encapsulation and axial anchoring within the coil case 13 and its global encapsulation and anchoring within the coil case 13 and the attachment 19, the reinforcement 16 of the third embodiment of the antenna coil assembly 10 responds to non-orthogonal impact forces ($F_A$) applied to the antenna coil assembly 10 by absorbing the lateral tensile force components thereof ($F_L$) that might otherwise be capable of fracturing or breaking the coil wire of the antenna 12.

The fourth of the several embodiments of the present invention possessing the non-orthogonal impact force resistant features is illustrated in FIGS. 13-15 and will be described using the same reference numerals previously used for similar structural elements of the first embodiment. As depicted, the antenna coil 12 of the fourth antenna assembly 10 comprises multifilament metallic wire 14 formed into three turns 12', 12" and 12'".

While the manner of axially attachment of the free ends 12a and 12b within an adjacent feedthrough case 20 is not illustrated in FIGS. 13-15, it is to be understood that the same or similar attachment mechanism may be employed in the fourth embodiment of the antenna coil assembly 10 (including the connection of the free end 12a of the wire 14 to the feedthrough pin 24 and the connection of the free end 12b of the wire 14 to the feedthrough pin 34). The previously described loops 12L-1 and 12L-2 are formed in the coil wire 14 to provide for axial movement of the wire 14 in response to external impact forces resisting the development of tensile forces sufficient to damage or fracture the wire 14.

As illustrated in each of FIGS. 13-15, the fourth non-orthogonal force absorbing reinforcement 16 of the fourth embodiment of the antenna coil assembly 10 of the present invention comprises a flat mesh 16m formed of a polymeric material such as a polyester or polypropylene mesh of cross connected members located on the top of and/or on the bottom of the wire 14 of the antenna coil 12 within the encapsulation 18 forming the coil case 13 as well as the feedthrough case 20 comprising the attachment 19. Thus positioned and encapsulated, the mesh 16m comprising the fourth embodiment of the reinforcement 16 is axially and laterally secured to absorb external impact forces, particularly non-orthogonal forces applied to the antenna coil assembly 10 that might otherwise be reflected as undesired tensile forces in the wire 14 of the antenna coil 12. The mesh is preferably of a configuration that is less prone to stretching, such as tightly woven instead of loosely knit.

Because the cross-connected members of the mesh 16m of the fourth embodiment of the reinforcement 16 of antenna coil assembly 10 and the individual fibers thereof are encapsulated within the polymer 18 and axially and laterally secured against stretching within the coil case 13 and within the feedthrough case 20 comprising the attachment 19, the mesh 16m resists axial movement in response to the lateral components of non-orthogonal impact forces applied to the assembly 10 as diagrammatically depicted in FIG. 2. As previously described and as there illustrated, a non-orthogonal impact force $F_A$ is applied to the antenna coil case 13. The non-orthogonal impact force $F_A$ comprises a lateral component $F_L$ and a normal component $F_N$. The lateral component $F_L$ is reflected in the plane of the coil 12 as a tensile force that might be capable of fracturing or breaking the antenna coil wire. However, in the antenna coil assembly 10 of the present invention, that lateral force component is absorbed by the reinforcement 16 encapsulated with the antenna coil 12 within the coil case 13. Specifically, in the fourth embodiment of the antenna coil assembly 10 illustrated and described above relative to FIGS. 13-15, the reinforcement 16 comprising the mesh 16m is structured and secured to resist axial movement within the coil case 13 whereas the antenna coil 12 is structured and allowed by the reinforcement some longitudinal movement within the coil case 13 and within the feedthrough case 20. Therefore, by virtue of its previously described internal structure and its local encapsulation and axial anchoring within the coil case 13 and its global encapsulation and anchoring within the coil case 13 and the attachment 19, the reinforcement 16 of the fourth embodiment of the antenna coil assembly 10 responds to non-orthogonal impact forces ($F_A$) applied to the antenna coil assembly 10 by absorbing the lateral tensile force components thereof ($F_L$) that might otherwise be capable of fracturing or breaking the coil wire of the antenna 12.

While in the foregoing, preferred embodiments of the present invention and preferred modes of operation thereof have been described and illustrated in detail, changes and modifications may be made without departing from the spirit of the present invention. Accordingly the present invention is to be limited in scope only by the following claims.

The invention claimed is:

1. An impact resistant implantable antenna assembly, comprising:
    a flat antenna coil comprising turns of conductive wire, wherein the turns of conductive wire in the antenna coil are laterally separated;
    a fiber bundle disposed parallel with the conductive wire and positioned between the laterally separated turns of the conductive wire;
    an attachment external to the antenna coil comprising a feedthrough case wherein the feedthrough case comprises laterally extending guide channels for receiving the ends of the wire and anchors for the fiber bundle, wherein ends of the fiber bundle are axially anchored to the attachment; and
    a flexible polymer encapsulating the antenna coil and the fiber bundle.

2. The antenna assembly of claim 1, wherein the anchors comprises anchor posts extending from the feedthrough case.

3. The antenna assembly of claim 1, wherein the guide channels in the feedthrough case comprise outwardly extending service loops in the plane of the feedthrough case, in which the service loops provide axial slack in the wire.

4. The antenna assembly of claim 3, further comprising a silicone tube, the wire passing through the silicone tube; wherein the wire moves in the silicone tube in response to lateral forces applied to the coil by an externally applied non-orthogonal impact force, the movement of the wire comprising straightening the wire in the service loops and translation of the wire with respect to the silicone tube.

5. The antenna assembly of claim 1, wherein lateral forces applied in the plane of the antenna coil are resisted by the fiber bundle and transmitted by the fiber bundle to the attachment, thereby preventing tensile stress in the wire from causing failure of the wire.

6. The antenna assembly of claim 1, wherein the conductive wire comprises more axial slack than the fiber bundle to allow the conductive wire to move in response to an non-orthogonal impact force without exceeding a tensile strength of the wire, wherein the fiber bundle has less axial slack than the conductive wire and is configured to resist axial stretching such that the fiber bundle resists deformation caused by the non-orthogonal impact force.

7. The antenna assembly of claim 1, further comprising a metal shield comprising a conductive wire wound perpendicularly around the conductive wire and fiber bundle to prevent capacitive coupling through tissue covering the antenna coil.

8. The antenna assembly of claim 1, wherein the antenna assembly is flexible in a region including the antenna coil, such that the antenna coil conforms to contours of surrounding biological tissue.

9. The antenna assembly of claim 1, wherein the fiber bundle is positioned laterally adjacent to, and in plane with, the turns of conductive wire.

10. The antenna assembly of claim 9, wherein the fiber bundle is spaced between the turns of conductive wire, wherein the flexible polymer fills a space between the fiber bundle and the turns of conductive wire.

11. The antenna assembly of claim 9, wherein the fiber bundle is laterally centered in a space between two adjacent turns of the conductive wire.

12. The antenna assembly of claim 1, wherein the fiber bundle comprises at least one of: polyester, polypropylene, or polyethylene fibers, in which the fibers are formed into a bundle with a stitch count selected to minimize axial stretching.

13. The antenna assembly of claim 1, wherein fibers in the fiber bundle are twisted together.

14. The antenna assembly of claim 1, wherein the fibers in the fiber bundle are braided.

15. The antenna assembly of claim 1, wherein the fiber bundle comprises 55 dtex fibers of ultra high molecular weight polyethylene, wherein eight fibers are braided together in a stitch count that resists axial stretching.

16. The antenna assembly of claim 1, wherein the fiber bundle is adhered to the conductive wire by the flexible polymer.

17. The antenna assembly of claim 1, wherein the bundle of polymer fibers is separate from the wire, wherein the ends of the bundle of polymer fibers are connected to anchor posts and ends of the wire are connected to feedthrough pins.

18. An impact resistant implantable antenna coil assembly comprising:
  an antenna coil having multiple turns of wire encapsulated within a flat, flexible protective coil case of biocompatible material;
  a non-orthogonal force absorbing reinforcement comprising a fiber bundle of a polymeric material laterally spaced between the turns of the wire and encapsulated and axially secured in the biocompatible material; and,
  an adjacent attachment wherein ends of the wire and the fiber bundle are axially secured to the adjacent attachment.

19. The antenna assembly of claim 18, wherein the fiber bundle is separate from the wire, wherein the ends of the fiber bundle are connected to anchor posts and ends of the wire are connected to feedthrough pins.

20. The antenna assembly of claim 18, wherein the wire comprises more axial slack than the fiber bundle to allow the wire to move in response to a non-orthogonal impact force without exceeding a tensile strength of the wire, wherein the fiber bundle has less axial slack than the wire and is configured to resist axial stretching such that the fiber bundle resists deformation caused by the non-orthogonal impact force.

21. The antenna assembly of claim 18, wherein lateral forces applied in the plane of the antenna coil are resisted by the fiber bundle and transmitted by the fiber bundle to the attachment, thereby preventing tensile stress in the wire from causing failure of the wire.

22. An impact resistant implantable antenna coil assembly, comprising:
  a flat antenna coil comprising a multiple turn spiral of conductive wire, wherein turns of conductive wire are laterally separated;
  a bundle of polymer fibers spirally coiled parallel to, and laterally spaced from, the wire; wherein the bundle of polymer fibers is in plane with the flat antenna coil and disposed between turns of the wire;
  an attachment comprising a feedthrough case with two anchor posts, wherein a first end of the bundle of polymer fibers passes around a first anchor post and a second end of the bundle of polymer fibers passes around a second anchor post, wherein the two anchor posts anchor the bundle of polymer fibers against non-orthogonal impact forces applied to the antenna coil assembly;
  laterally extending guide channels for receiving ends of the wire, the guide channels comprising outwardly extending loops in plane with the feedthrough case, the outwardly extending loops allowing limited motion of the wire to relieve tensile stress in the wire, wherein deformation of the antenna coil produced by non-orthogonal forces is resisted by the bundle of polymer fibers, thereby preventing tensile stress in the wire from causing failure of the wire; and
  a flexible polymer encapsulating the antenna coil and the bundle of polymer fibers;
  wherein the antenna coil assembly is flexible in a region including the antenna coil.

* * * * *